United States Patent [19]

Arkles et al.

[11] Patent Number: 4,711,820

[45] Date of Patent: Dec. 8, 1987

[54] METHOD OF SILICONIZATION OF SURFACES WITH LOWER ALKYL SILANES

[75] Inventors: Barry C. Arkles, Ambler; William S. Brinigar, Bala Cynwyd, both of Pa.

[73] Assignee: Petrarch Systems Inc., Bristol, Pa.

[21] Appl. No.: 875,149

[22] Filed: Jun. 17, 1986

[51] Int. Cl.$^4$ ............... C03C 17/00; C03C 25/02; B32B 9/04; B32B 17/06

[52] U.S. Cl. .................. 428/429; 65/60.3; 428/447

[58] Field of Search ............. 65/60.3; 427/164, 165, 427/167, 169, 389.7, 2; 428/429, 447

[56] References Cited

U.S. PATENT DOCUMENTS

| | | | |
|---|---|---|---|
| 3,317,369 | 5/1967 | Clark et al. ............... | 428/429 X |
| 3,395,069 | 7/1968 | Plueddemann ............ | 428/429 X |
| 4,235,654 | 11/1980 | Dohi et al. ............... | 65/60.3 X |
| 4,263,350 | 4/1981 | Valimont .................. | 428/429 X |
| 4,338,375 | 7/1982 | Hashimoto et al. ....... | 428/429 X |

FOREIGN PATENT DOCUMENTS 752621  12/1970  Belgium ...................... 65/60.3

*Primary Examiner*—Michael H. Lusignan
*Attorney, Agent, or Firm*—Panitch Schwarze Jacobs and Nadel

[57] ABSTRACT

A method of treating a surface to be contacted by a protein-containing fluid reduces protein adsorption to the surface. The method comprises coating or siliconizing the surface with a lower alkyl silane selected from the group consisting of monoalkyl silanes of the formula $RSiX_3$ wherein R is selected from ethyl and branched ($C_3$-$C_5$) alkyl and X is selected from hydrolyzable groups, such as halogen or lower alkoxy, and dialkyl silanes of the formula $R'_2SiX_2$ wherein R' is ($C_2$-$C_5$) alkyl and X is as described above. For example, borosilicate glass vessels for storing blood may be treated.

20 Claims, No Drawings

METHOD OF SILICONIZATION OF SURFACES WITH LOWER ALKYL SILANES

BACKGROUND OF THE INVENTION

The present invention relates generally to a method of treating a surface to impart a controlled hydrophobic character; and more particularly to a method of treating a surface with a silicon-containing compound to control the hydrophobicity of the surface and to reduce the adsorption of protein.

"Siliconization" is defined to be the imparting of silicone-like properties to a substrate material by addition or reaction of silicon containing compounds with the substrate resulting in the formation of a thin surface film. At times siliconization is used merely to obtain a hydrophobic surface. However, often the objective of siliconization is to prevent undesired interaction between the surface and biological macromolecules. While the biocompatibility of silicone elastomers has been well examined, siliconized substrate materials demonstrate a broader range of bio-interaction.

Although materials intended for applications such as implants and invasive and extracorporeal support devices have been well studied, materials which have "ex vivo" contact with biological tissues have been largely ignored. While substrate siliconization is employed in a variety of analytical techniques, and glass contacting surfaces are often siliconized, blood contact with glass has been generally overlooked. Siliconized surfaces in general exhibit a low level of interaction with "blood fluids," which are defined to include whole blood, components thereof, and products prepared therefrom including blood fractions, and other protein-containing fluids, yet that interaction may be critical for subsequent diagnostic analysis of blood fluids and other protein-containing fluids stored in glass. As a rule, accurate diagnostic tests require minimal interaction between the glass storage or transfer vessel and the blood fluid.

The interaction of blood with foreign surfaces such as the walls of storage containers or the surfaces of implants, in the absence of inhibitors, is a rapid series of events sensitive to a variety of factors. Foreign surfaces ideally should resemble vascular endothelia which provide a nonthrombogenic surface resistant to platelet adhesion and aggregation. However, biomaterials generally present non-ideal surfaces. Consequently, exposure to the biomaterial surface may trigger a thrombogenic cascade in the blood. Plasma proteins are adsorbed and platelets and leukocytes adhere to the surface. Platelets are activated by a release reaction and recruitment of nearby platelets with the eventual formation of the thrombus. Subsequently, formation of crosslinked fibrin stabilizes the thrombus. In addition, complement activation may occur mediating a long term immunological response to the surface.

Another important factor is the tendency of some surfaces to lyse erythrocytes. While erythrocytes represent only 40 percent of blood in terms of packed cell volume, erythrocytes contain 140 milligrams hemoglobin protein per milliliter whole blood, and less than 0.01 mg/ml of hemoglobin is found in the plasma. Thus, a biomaterial surface which causes hemolysis raises the level of free blood protein and effects a profound change in blood characteristics.

An ideal biomaterial surface would not activate the thrombogenic cascade, the complement system, or cause hemolysis. Because protein adsorption is important in initiating the thrombogenic cascade and in complement activation, and because minimal interaction of blood fluid with the containers in which it is stored is generally desirable for diagnostic test accuracy, there is a clear need for a siliconization technique which minimizes adsorption of protein from blood fluids.

BRIEF SUMMARY OF THE INVENTION

The present invention provides a method of siliconization of a surface to be contacted by a blood fluid to reduce blood protein adsorption on the surface. The method comprises contacting the surface with a lower alkyl silane selected from the group consisting of monoalkyl silanes of the formula $RSiX_3$, wherein R is selected from ethyl and branched ($C_3$–$C_5$) alkyl and X is selected from the group consisting of halogen, alkoxy and other hydrolyzable groups, preferably small (e.g. lower alkoxy) hydrolyzable groups; and dialkyl silanes of the formula $R'_2SiX_2$, wherein R' is ($C_2$–$C_5$) alkyl and X is as described above.

The method of the present invention provides siliconized surfaces which exhibit a surprising and unexpected reduction in the adsorption of blood protein. Borosilicate glass surfaces, such as the interior surfaces of glass storage vessels and the like, may be treated according to the present method to reduce the adsorption of proteins from blood fluids which are stored in the glass vessels and contact the treated surfaces. Lower alkyl silanes which may be used in the method include t-butyltrichlorosilane and di-n-propyldichlorosilane.

DETAILED DESCRIPTION OF THE PREFERRED EMBODIMENTS

The use of alkylsiloxane agents to convert hydrophilic surfaces to water repellant, lower energy, hydrophobic surfaces is known in treatments for masonry, electrical insulators, packings for chromotography and in non-caking fire extinguishing materials. For example, trimethylchlorosilane and other volatile alkyl-siloxane agents have been used to treat silica packings for gas-liquid chromatography (GLC) columns, thin layer chromotography (TLC) plates, and packings for reversed phase high performance liquid chromotography (HPLC) columns.

There are a number of clinical diagnostic tests in which it is important to minimize interaction between the surface of the glass storage container and protein which participates in the test. For example, in certain diagnostic tests related to hepatic function, such as the measurement of the activity of glutamic oxaloacetic transaminase (GOT) and glutamic pyruvic transaminase (GPT), it is important to measure the enzyme activity quickly. Prompt measurement to avoid reaction with glass surfaces is also important in immune system diagnostic tests, such as tests for the complement factors $C_3$ and $C_4$, as well as various immunoglobins. Relevant diagnostic test methods are reviewed in I. Davidsohn et al., *Clinical Diagnosis by Laboratory Methods* (15th Ed. W. B. Saunders Company Philadelphia).

The present invention promotes more accurate testing and increased test scheduling flexibility by reducing protein-glass surface interaction. Similarly, in situations in which diagnostic tests cannot be performed immediately, such as when samples are collected from patients in remote locations, the reduced protein-glass surface interaction provided by the present invention increases diagnostic test accuracy.

A variety of techniques have been used to siliconize surfaces. For example, poly(dimethylsiloxane) itself has been used as a surface coating material, either neat or in solution. Poly(dimethylsiloxane) in an aqueous emulsion form has also been used. After application, the poly(dimethylsiloxane) may be permitted simply to dry or it may be baked to provide a siliconized surface. Similarly, chlorine-terminated poly(dimethylsiloxane) oligomers may be dissolved in an aprotic solvent to form a siliconization treatment solution.

Siliconization may also be achieved by using an octadecylsilsesquioxane-based coating material. For example, an aqueous dispersion of silane micelles can be prepared by diluting a solution of octadecyltrialkoxysilane in t-butanol and diacetone alcohol. Surfaces may be siliconized by dipping in the aqueous dispersion and subsequently curing.

Methylated chlorosilanes such as dimethyldichlorosilane and trimethylchlorosilane have also been used to siliconize surfaces. However, as discussed below, while methylated chlorosilanes are somewhat effective in imparting a hydrophobic character to the surface treated, they are unexpectedly less effective in producing siliconized surfaces which exhibit reduced blood protein adsorption than the lower alkylsilanes employed in the present method.

In general, the lower alkyl silanes which can be employed in the present method include monoalkyl silanes of the formula $RSiX_3$ wherein R is selected from ethyl and branched ($C_3$-$C_5$) alkyl. In general, X can be any functional group which forms a hydrolyzable bond to silicon, including particularly halogen and alkoxy. Preferably, X is halogen. Further, the lower alkyl silanes which can be used include dialkyl silanes of the formula $R'_2SiX_2$ wherein R' is ($C_2$-$C_5$) alkyl and X is as described above.

Non-limiting examples of lower alkyl silanes which may be employed in the method of the present invention include diisopropyldichlorosilane, diethyldiethoxysilane, diethylmethoxychlorosilane, isopropyl-t-butyldibromosilane, isopropyltrichlorosilane, t-butyltrichlorosilane, di-t-butyldichlorosilane, diethyldichlorosilane, di-n-propyldichlorosilane, ethyltrichlorosilane and ethyltriiodosilane. Mixtures of two or more lower alkyl silanes can also be employed in the present method. For example, a mixture of diisopropyldichlorosilane and t-butyltrichlorosilane can be used.

The surface which is to be treated can be contacted with a lower alkyl silane in the form of a neat liquid or vapor. Alternatively, the lower alkyl silane can be dissolved in a solvent. Examples of suitable solvents include alcohols such as methanol, ethanol, and isopropanol; ethers such as diethyl ether; hydrocarbons such as hexane and toluene; halogenated hydrocarbons such as methylene chloride; and other aprotic organic solvents such as dimethylformamide. The choice of a solvent may depend on the interaction between the solvent and the surface to be treated. The concentration of the lower alkyl silane in the treatment solution depends on a number of factors such as the rate of treatment, the mode of application, and the like.

Preferably, the lower alkyl silane is dissolved in an aprotic or hydroxylic solvent such as tetrahydrofuran or ethanol at a concentration of from about 5 to 100 g/l. The temperature of application depends on the rate of reaction of the lower alkyl silane and the surface. In general, the temperature and concentration of the lower alkyl silane are not critical, and the surface to be treated can be exposed for a relatively short period, such as about 1–5 minutes when a borosilicate glass surface is to be treated with a dilute solution of the lower alkyl silane at a temperature of about 30 degrees C. to 40 degrees C. and having about 20 g of silane per 1000 g of solvent. If desired, the reaction can be carried out at room temperature (25 degrees C.).

Surfaces can also be treated by immersing them in the silane at reflux, or by exposing them to silane vapor at elevated temperature or in a glow discharge.

The surface treated by the present invention can be a surface which has a functional group capable of reaction with the lower alkyl silanes employed in the present method. For example, glass surfaces having silanol functional groups can be treated by the present method. Synthetic polymer surfaces, such as polyurethane, which are chemically reactive with the lower alkyl silanes employed in the present method can be treated also. As is recognized in the art, halogenated silanes such as the alkyl silanes of the present invention are reactive with "active" hydrogen. Thus, for example, synthetic polymer surfaces which possess active hydrogen containing functional groups such as alcohol, amine, carboxylic acid, phenol, and the like, can be treated according to the present invention. Further, surfaces which adsorb the lower alkyl silanes of the present invention or polymerization, oligomerization, or condensation products thereof can be treated.

Materials which can be treated by the method of the present invention include materials used in clinical implants, such as low temperature isotropic (LTI) carbon, segmented polyether-urethanes, polyurethane-polyorganosiloxane block copolymers, segmented copolyether-imides, ethyl cellulose, polyamides, and polyamide-polyether block copolymers; as well as materials employed ex vivo, such as N,N'-diethylamino cellulose employed in membranes, collagen-chondroitin-6 sulfate composites used in making tubing, methylmethacrylate-grafted collagen, and the like.

In addition to use in treating blood collection vessels and storage container surfaces, the present method can be used to treat surfaces of vessels in which blood is processed prior to diagnostic testing. For example, centrifuge tubes, pipettes, spectrophotometer cells and the like can be treated. Similarly, the interior surfaces of microanalytical automated testing apparatus can be treated. The present method may be especially beneficial in treating blood fluid contacting surfaces of vessels in which diagnostic tests relating to blood protein characteristics are carried out.

A by-product of the silylation of a surface with a halogenated lower alkyl silane is a hydrohalic acid. For example, when a vitreous surface is treated by the present method with t-butyltrichlorosilane, hydrochloric acid is a by-product. Thus, in addition to the lower alkyl silanes of the present invention, a proton acceptor such as ammonia, triethylamine, pyridine or hexamethyldisilazane may be dissolved in the treatment solution.

While not wishing to be bound by a particular theory or explanation of the result of treatment according to the present method, it is believed that a layer of poly(alkylsiloxane), probably in the form of oligomers, is formed on the treated surface by the present method. A monolayer or thicker layer of poly(alkylsiloxane) may be formed. The chemical nature of the silane-glass interface is discussed in E. P. Plueddemann, *Silane Coupling Agents* (Plenum Press, N.Y. 1982) 75–108.

The following specific examples illustrate presently preferred methods for practicing the invention, without however being limited thereto.

In order to assess surfaces treated according to the present invention as blood fluid-contacting surfaces for biomaterials, siliconized vitreous surfaces were tested for hemolysis and blood protein adsorption from whole human blood. The contact angle of water on the treated surfaces was also measured. In addition, comparative measurements were made of the hemolysis, blood protein adsorption and contact angle of a number of surfaces siliconized by prior art methods.

KIMAX (registered trademark of Owens-Illinois Inc.) borosilicate glass tubes were employed in the hemolysis and blood protein absorption studies. PYREX (registered trademark of Corning Glass Company) borosilicate glass slides were used in measuring contact angles. Both borosilicate glass tubes and borosilicate glass slides were treated with 5 percent w/w hydrochloric acid for 24 hours and then thoroughly rinsed with distilled water prior to siliconization.

The contact angle of water on siliconized glass slides was determined by goniometer. Several determinations of the spreading and receding contact angles were made and averaged.

Blood was freshly drawn from volunteers into evacuated B-D vacutainers containing sodium citrate. In measuring hemolysis, approximately one milliliter of whole blood, which was drawn in heparin, was added to each siliconized test tube studied. A pediatric red top vacutainer coated with "silicone (B-D)" was used as a control. Day zero plasma was obtained and stored in microhematocrit capillary tubes sealed at one end with CRITOSEAL (registered trademark of Sherwood-Lancer) material. Samples on subsequent days were drawn into microhematocrit capillary tubes, peripheral blood smears were obtained, and the tubes were next centrifuged in an AUTOCRIT (registered trademark of Clay-Adams) centrifuge. The tubes were scored and snapped at the packed cell/plasma interface, and the plasma was stored in the tube which was resealed at one end with CRITOSEAL material. The amount of Hb in the plasma was determined according to the method of Levinson and Goldman, *Clinical Chemistry* 28, 417 (1982).

Either one or two microliters of plasma was added to 100 microliters of 3,3′,5,5′-tetramethylbenzidine (Aldrich Chemical Co.) in 90 percent (v/v) acetic acid. After addition of 100 microliters 0.1 percent hydrogen peroxide (v/v), the samples were incubated for twenty minutes before diluting with either one or two milliliters 10 percent (v/v) acetic acid. The adsorption of samples at 660 nanometers was then determined. A standard curve was prepared with each assay. The whole blood samples were stored in a 4 degree C. cold room throughout the study.

Blood protein adsorption was studied as follows: Blood was dispensed into siliconized tubes and stored at 4 degrees C. for 72–100 hours. The blood was then agitated with a vortex mixer and aspirated. Saline solution was added to displace adsorbed blood protein and the tube was inverted 2–3 times and aspirated. Saline addition was repeated twice and a Biuret analysis for protein was made as described in A. G. Gornall, C. J. Baradawill, M. M. David, *J. Biol. Chem.*, 177, 751 (1949). This process was elected over the Coomassie blue technique since the basic condition of the former technique facilitates debonding of organic silicon compounds, thus releasing proteins. The Coomassie blue technique did not debond proteins and gave false positive results for protein on siliconized surfaces having long chain alkyl groups. Bovine serum albumin was employed for calibration. The average adsorption from 530 to 515 nanometers was determined on a Hewlett Packard UV/VIS model 8450A spectrophotometer.

EXAMPLE 1

A two percent (w/w) solution of t-butyltrichlorosilane in warm (40–60 degrees C.) ethanol was prepared. The borosilicate glass substrates were dipped in the solution several times to insure even wetting. Total immersion time was 10–15 minutes. The substrates were then rinsed once with ethanol and allowed to air dry before being placed in an oven at 105 degrees C. for 3–5 minutes. The contact angle, blood hemolysis, and blood protein adsorption of the siliconized substrates were measured as discussed above. The results are reported in Table I.

EXAMPLE 2

A two percent (w/w) solution of di-n-propyldichlorosilane in warm (40–60 degrees C.) ethanol was prepared and the borosilicate glass substrates were siliconized as in Example 1.

COMPARATIVE EXAMPLES 1 and 2

Two percent solutions of trimethylchlorosilane and dimethyloctadecylchlorosilane in warm (40–60 degree C.) ethanol were prepared. Borosilicate glass substrates were siliconized following the same procedure as described in Example 1.

COMPARATIVE EXAMPLE 3

A solution of GLASSCLAD (registered trademark of Petrarch Systems Inc.) 18 solution, a 20 percent octadecyltrialkoxysilane (octadecylsilsesquioxane) concentrate in a solution of t-butanol and diacetone alcohol was prepared as a 1 percent (w/w) solution in distilled water to give an active concentration of 0.2 percent (w/w) octadecylsilane. Borosilicate glass surfaces were then immersed 5–10 seconds with gentle agitation and subsequently dipped briefly into distilled water. The coating was cured at 105 degrees C. for 2 minutes.

COMPARATIVE EXAMPLE 4

A chlorinated siloxane oligomer siliconization was effected by preparing a 5 percent (w/w) hexane solution of a chlorine-terminated dimethylsiloxane oligomer mixture containing primarily trisiloxane and tetrasiloxane and designated GLASSCLAD 6C. Borosilicate glass surfaces were immersed for 15 minutes in the hexane solution and then cured for 20 minutes at 105 degrees C. Subsequently, the siliconized substrates were rinsed with alcohol and dried.

COMPARATIVE EXAMPLE 5

Siliconization with a hydrophilic silane was effected by first preparing a mixture of 2 percent (w/w) N-trimethoxysilylpropyl-N,N,N-trimethylammonium chloride and 5 percent (w/w) water in methanol mixture. This solution was warmed to 30–40 degrees C. and borosilicate glass surfaces were immersed in the solution for 5–10 minutes. The siliconized surfaces were then dried for 5 minutes at 105 degrees C. and rinsed with methanol.

The contact angle of water, hemolysis and blood protein adsorption of each of the siliconized surfaces were measured as described above. The results of these measurements are reported in Table I.

non-polar structures such as those provided by the dimethyloctadecylchlorosilane treatment (Comparative Example 2) permit extended hydrophobic interaction with proteins, increasing protein adsorption.

TABLE I

| | Siliconization Agent | Contact Angle* | Relative Hemolysis Day 1 | Day 4 | Relative Protein Adsorption (microgram protein/ 100 sq. mm) |
|---|---|---|---|---|---|
| Example 1 | di-n-propyldichlorosilane | 62–80 | 1.0 | 2.6 | 2 |
| Example 2 | t-butyltrichlorosilane | 67–73 | 1.3 | 2.0 | 4 |
| Comparative Example 1 | trimethylchlorosilane | 76–85 | 0.8 | 1.2 | 8 |
| Comparative Example 2 | dimethyloctadecylchlorosilane | 65–85 | — | — | 40–60 |
| Comparative Example 3 | octadecylsilsesquioxane | 65–100 | 0.7 | 1.5 | 6 |
| Comparative Example 4 | chlorinated dimethyl siloxane | 75–90 | 0.8 | 2.4 | 20–25 |
| Comparative Example 5 | N—trimethyloxysilylpropyl-N,N,N—trimethylammonium chloride | 10–20 | 1.2 | 3.5 | 20–50 |
| Control | untreated | — | 1.0 | 3.5 | — |

*The first figure represents the spreading contact angle and the second figure represents the receding contact angle.

As indicated in Table I, all siliconization techniques (except Comparative Example 5) produced hydrophobic surfaces, although considerable variability in the degree of hydrophobicity was shown. The chlorinated siloxane oligomer-treated surface (Comparative Example 4) and the octadecylsilsesquioxane-treated surface (Comparative Example 3) exhibited the greatest range of contact angles, but were generally the most hydrophobic of the surfaces evaluated. The silylated ammonium quat (Comparative Example 5) was an exception, giving the only readily wettable surface.

All siliconization surface treatments elicited extremely low levels of hemolysis, less than 0.05 percent. The results reported in Table I are given relative to a 5 percent HCl washed, deionized water rinsed control. The plasma level of hemoglobin at day one for the control was defined as 1. By day four all surface treatments except for the siliconization with the ammonium quat (Comparative Example 5) demonstrated less hemolysis than the untreated control.

As reported in Table I, the ammonium quat silane-treated surface (Comparative Example 5) and the dimethyloctadecylchlorosilane-treated surface (Comparative Example 2) exhibited the highest level of protein adsorption. The octadecylsilsesquioxane treatment (Comparative Example 3) produced one of the lowest levels of protein adsorption. Surprisingly, however, the least protein adsorption was observed with the surfaces siliconized by the process of the present invention, namely the di-n-propyldichlorosilane-treated surface (Example 1) and the t-butyltrichlorosilane-treated surface (Example 2). Only one-fourth as much protein was found to adsorb to the di-n-propyldichlorosilane-treated surface as did to the trimethylchlorosilane-treated surface. Similarly, only half as much protein was found to adsorb to the t-butyltrichlorosilane-treated surface as did to the trimethylchlorosilane-treated surface.

While not wishing to be bound to a particular theory or explanation of these results, it is believed that siliconization by the process of the present invention yields surfaces which exhibit relatively low protein adsorption compared with higher alkyl silanes because the alkyl groups bonded to the substrate surface are relatively closed sterically and do not extend far from the substrate surface. Both of these factors are believed to reduce the opportunity for extended hydrophobic interaction with proteins. On the other hand, long chain non-polar structures such as those provided by the dimethyloctadecylchlorosilane treatment (Comparative Example 2) permit extended hydrophobic interaction with proteins, increasing protein adsorption.

The present invention may be embodied in other specific forms without departing from the spirt or essential attributes thereof, and, accordingly, reference should be made to the appended claims, rather than the foregoing specification, as indicating the scope of the invention.

We claim:

1. A method of treating a surface to be contacted by a protein-containing fluid to reduce protein adsorption to the surface, the method comprising coating the surface with a lower alkyl silane selected from the group consisting of monoalkyl silanes of the formula $RSiX_3$, wherein R is selected from ethyl and branched ($C_3$–$C_5$) alkyl and X is a hydrolyzable group, and dialkyl silanes of the formula $R'_2SiX_2$, wherein R' is ($C_2$–$C_5$) alkyl and X is as described above.

2. A method according to claim 1 wherein the surface is selected from glass and synthetic polymer surfaces.

3. A method according to claim 2 wherein the synthetic polymer surface is hydrophilic.

4. A method according to claim 2 wherein the surface is a borosilicate glass surface.

5. A method according to claim 1 wherein the hydrolyzable is chlorine.

6. A method according to claim 5 wherein the lower alkyl silane is di-n-propyldichlorosilane.

7. A method according to claim 5 wherein the lower alkyl silane is t-butyltrichlorosilane.

8. A method according to claim 1 wherein the hydrolyzable group is selected from the group consisting of halogen and ($C_1$–$C_3$) alkoxy.

9. A method according to claim 1 wherein the lower alkyl silane is disolved in solvent to form a solution prior to contacting the surface.

10. A method according to claim 9 wherein the solvent is ethanol and the solution is maintained at a temperature of from about 40 degrees C. to 60 degrees C. while contacting the surface.

11. A surface treated according to the method of claim 1.

12. A surface treated according to the method of claim 2.

13. A surface treated according to the method of claim 3.

14. A surface treated according to the method of claim 4.

15. A surface treated according to the method of claim 5.

16. A surface treated according to the method of claim 6.

17. A surface treated according to the method of claim 7.

18. A surface treated according to the method of claim 8.

19. A surface treated according to the method of claim 9.

20. A surface treated according to the method of claim 10.

* * * * *